United States Patent
Cohen

(10) Patent No.: US 11,696,818 B2
(45) Date of Patent: Jul. 11, 2023

(54) ONLINE, REAL-TIME MASS VACCINATION AND DATA COLLECTION SYSTEM

(71) Applicant: SyrinJector Ltd., Petah Tikva (IL)

(72) Inventor: Nahum Cohen, Ashdod (IL)

(73) Assignee: SyrinJector Ltd, Petach Tikva (IL)

( * ) Notice: Subject to any disclaimer, the term of this patent is extended or adjusted under 35 U.S.C. 154(b) by 684 days.

(21) Appl. No.: 16/461,404

(22) PCT Filed: Nov. 16, 2017

(86) PCT No.: PCT/IL2017/051254
§ 371 (c)(1),
(2) Date: May 16, 2019

(87) PCT Pub. No.: WO2018/092138
PCT Pub. Date: May 24, 2018

(65) Prior Publication Data
US 2019/0343610 A1    Nov. 14, 2019

Related U.S. Application Data

(60) Provisional application No. 62/423,216, filed on Nov. 17, 2016.

(51) Int. Cl.
*A61D 1/02* (2006.01)
*A61D 7/00* (2006.01)
(Continued)

(52) U.S. Cl.
CPC ............... *A61D 1/025* (2013.01); *A61D 7/00* (2013.01); *A61M 5/14546* (2013.01);
(Continued)

(58) Field of Classification Search
CPC .... A61M 2202/30; A61M 5/425; A61M 5/44; A61M 5/46; A61M 5/14546;
(Continued)

(56) References Cited

U.S. PATENT DOCUMENTS

| 3,949,746 A | 4/1976 | Wallach |
| 5,080,648 A * | 1/1992 | D'Antonio .......... A61M 5/2425 604/71 |

(Continued)

FOREIGN PATENT DOCUMENTS

| CN | 1374135 A | 10/2002 |
| CN | 201186088 Y | 1/2009 |

(Continued)

OTHER PUBLICATIONS

Supplementary European Search Report for corresponding European application 17871482.0 dated Nov. 14, 2019.
(Continued)

*Primary Examiner* — Theodore J Stigell
(74) *Attorney, Agent, or Firm* — Heidi Brun Associates Ltd.

(57) ABSTRACT

A system for mass vaccination includes a plurality of portable electronic injectors, a mobile process manager and a database. Each portable electronic injector includes at least one needle to administer a measured amount of at least one vaccine to a body skin/tissue and an indicator system to provide an indication when either an injection error occurs or when a vaccination indication is required. The mobile process manager is in wireless communication with the plurality of injection devices and controls a mass vaccination. The process manager transmits task data to all injection devices in parallel via WI-FI, receives the vaccination indications from each injector in real time, also receives injection errors and vaccination process data, alerts a vaccination process overseer generally in real-time of the errors and transmits the injection data from each injector via cellular and/or internet transmission to the database.

29 Claims, 15 Drawing Sheets

(51) Int. Cl.
*A61M 5/145* (2006.01)
*A61M 5/158* (2006.01)
*A61M 5/168* (2006.01)
*A61M 5/172* (2006.01)
*A61M 5/42* (2006.01)
*A61M 5/44* (2006.01)
*A61M 5/46* (2006.01)

(52) U.S. Cl.
CPC ........ *A61M 5/158* (2013.01); *A61M 5/16886* (2013.01); *A61M 5/172* (2013.01); *A61M 5/425* (2013.01); *A61M 5/44* (2013.01); *A61M 5/46* (2013.01); *A61M 2005/14506* (2013.01); *A61M 2202/30* (2013.01); *A61M 2205/13* (2013.01); *A61M 2205/18* (2013.01); *A61M 2205/3368* (2013.01); *A61M 2205/3561* (2013.01); *A61M 2205/3584* (2013.01); *A61M 2205/50* (2013.01); *A61M 2205/52* (2013.01); *A61M 2205/587* (2013.01); *A61M 2205/6054* (2013.01); *A61M 2205/8206* (2013.01); *A61M 2209/06* (2013.01); *A61M 2250/00* (2013.01)

(58) Field of Classification Search
CPC .... A61M 5/16886; A61M 2005/14506; A61M 5/158; A61M 5/172; A61M 2205/13; A61M 2205/18; A61M 2205/3368; A61M 2205/3561; A61D 7/00; A61D 1/025; A61J 7/0053
See application file for complete search history.

(56) References Cited

U.S. PATENT DOCUMENTS

| | | | |
|---|---|---|---|
| 5,269,762 A | 12/1993 | Armbruster et al. | |
| 5,911,709 A * | 6/1999 | Hogan | A61D 1/025 222/529 |
| 6,264,637 B1 * | 7/2001 | Hogan | A61D 1/025 606/116 |
| 6,626,871 B1 | 9/2003 | Smoliarov | |
| 6,796,964 B2 | 9/2004 | Eidson et al. | |
| 6,858,020 B2 | 2/2005 | Rusnak | |
| 7,802,541 B2 | 9/2010 | Jones et al. | |
| 8,911,409 B2 * | 12/2014 | Clayton | A61B 90/30 433/29 |
| 2006/0247578 A1 | 11/2006 | Uedas et al. | |
| 2009/0024112 A1 | 1/2009 | Edwards et al. | |
| 2009/0171296 A1 * | 7/2009 | Fabian | A61M 5/3202 29/428 |
| 2011/0166509 A1 | 7/2011 | Gross et al. | |
| 2012/0203164 A1 | 8/2012 | Bitton et al. | |
| 2015/0174321 A1 * | 6/2015 | Cohen | A61M 5/1723 604/82 |

FOREIGN PATENT DOCUMENTS

| | | | |
|---|---|---|---|
| DK | 178609 B1 | | 8/2016 |
| WO | 2004101060 | | 11/2004 |
| WO | 2006091838 A2 | | 7/2008 |
| WO | 2016033507 | | 3/2016 |
| WO | WO-2016/033507 | * | 3/2016 |
| WO | 2016098060 | | 6/2016 |
| WO | 2016101031 | | 6/2016 |
| WO | WO-2016/101031 | * | 6/2016 |

OTHER PUBLICATIONS

English Abstract of CN 201187088Y downloaded on Mar. 8, 2018.
International Search Report for corresponding PCT application PCT/IL2017/051254 dated Mar. 5, 2018.

* cited by examiner

ONLINE, REAL-TIME MASS VACCINATION AND DATA COLLECTION SYSTEM

CROSS REFERENCE TO RELATED APPLICATIONS

This application is a national phase filing of PCT international application number PCT/IL2017/051254, having an international filing date of Nov. 16, 2017, published as international publication number WO 2018/092138, which in turn claims priority from U.S. provisional patent application 62/423,216, filed Nov. 17, 2016, both of which are incorporated herein by reference.

FIELD OF THE INVENTION

The present invention relates to mass vaccination devices generally and to an automatic mass vaccination device in particular.

BACKGROUND OF THE INVENTION

Vaccinations may be used to prevent and/or reduce the effects of diseases in living creatures. They may be administered in various stages of the life of a human or an animal, depending on the type of disease the vaccine is designed to prevent or treat. In poultry for example, some vaccines may be administered the first day a chick hatches, while others may be administered when the chicks are several weeks old, and in some cases when they are several months old.

Animal vaccination typically involves vaccinating many animals at a substantially same time. The animals may all be part of a same herd or flock, and may sometimes include animals from neighboring herds (or flocks), which may sometimes number into the hundreds and even the thousands. Mass vaccination devices are frequently used to perform these vaccinations; most of these devices are generally configured for automatic or semi-automatic operation.

An example of a mass vaccination device is described in WO 2004/101060 A2, "AUTOMATIC INJECTOR FOR MASS INJECTIONS", which describes "an injection assembly adapted to be carried by a user for mass injection of a medical material. The assembly comprises dosing unit (100.1) adapted to push predetermined doses of the medical material, propelling means adapted to actuate the dosing unit, means for supplying the medical material, controller (200), and automatic injector (500) that comprises housing, movable needle that can be housed or protruded to discharge the medical material received from the housing unit. Contact sensor and positioning sensor delivers information to the controller (200) and the controller (200) orders the propelling means as well as the dosing unit (100.1) and the needle to automatically push the medical material. The assembly can be provided with means for supplying antiseptic material to disinfect the needle between injections and in case of injecting humans, the assembly comprises a needle magazine so as to change the needles. The apparatus can be provided with electronically or physical marker for recording".

Another example is described in U.S. Pat. No. 6,796,964 B2, "AUTOMATIC VETERINARY MEDICAMENT DELIVERY SYSTEM", which describes "an electrically powered, plunger-free, valve-free adjustable veterinary delivery system for the administration of veterinary pharmaceuticals or vaccines to a variety of poultry or livestock. The delivery system includes a rechargeable battery positioned to power an electric motor which is used to actuate a peristaltic pump that propels pre-determined quantity of fluid medicament through the system for delivery. The system teaches adjustable dosage control of the fluid medicament by means of an electronic control unit which uses photo-optic sensor to calibrate dosage. The veterinary delivery system includes several hand-held injection devices from which to choose, depending on desired use, each having a push-button trigger, at least one needle, a headlight, signal lights, optional dye marking means, and an optional mixing chamber for mixing medicaments at the time of delivery of the medicament, the hand-held injection devices being easily connected and disconnected by means of quick connect fluid couplers for being in fluid communication with the system and a nine-pin amp electrical connector for being in electronic communication with the control unit".

A third example of a mass vaccination device is described in U.S. Pat. No. 7,802,541, "POULTRY VACCINATION APPARATUS AND METHOD", which describes "an apparatus for providing multiple vaccinations of poultry simultaneously is described. A neck injection, breast injection, two wing injections, and an eye mist or drop may be performed in one operation. The apparatus holds the bird in position for precise location of injections, thereby reducing wasted vaccine. The risk of injury to the bird during the process is minimized by greatly reducing the manual handling of the bird during vaccination. Vaccination costs are also reduced by the reduction of labor otherwise required in this process".

Other examples of mass vaccination devices are described in U.S. Pat. Nos. 3,949,746; 6,858,020; US 2006/0247578 A1; and U.S. Pat. No. 5,269,762.

Finally, US Patent Publication 2015/0174321, now issued as U.S. Pat. No. 10,384,003, assigned to the common assignee of the present invention, describes a multi-needle syringe for injecting multiple vaccines at once and for maintaining the quality of the vaccines.

SUMMARY OF THE PRESENT INVENTION

There is therefore provided, in accordance with a preferred embodiment of the present invention, a system for mass vaccination. The system includes a plurality of portable electronic injectors, a mobile process manager and a database. Each portable injector includes at least one needle to administer a measured amount of at least one vaccine to a body tissue and an indicator system to provide an indication when either an injection error occurs or when a vaccination indication is required. The mobile process manager is in wireless communication with the plurality of injection devices and controls a mass vaccination, receives the vaccination indications from each injection device in real time, the injection errors and vaccination process data and alerts a vaccination process overseer generally in real-time of the errors. The database is in internet and/or cellular communication with at least one mobile process manager and receives the vaccination indications, the injection errors and vaccination process data.

Moreover, in accordance with a preferred embodiment of the present invention, the mobile process manager is implemented on a smartphone, a tablet, or a computerized unit.

Further, in accordance with a preferred embodiment of the present invention, the wireless communication is a local WI-FI connection.

Moreover, in accordance with a preferred embodiment of the present invention, the mobile process manager downloads injection task parameters to the plurality of injectors in parallel. The task data includes but is not limited to: number of vaccines, dose of each vaccine, farmer data, injection device operators' names, number of injection per needle etc.

Additionally, in accordance with a preferred embodiment of the present invention, each injector device has an associated user unit on which is mounted an indicator light which lights up when one of the vaccination indications or injection errors occurs.

Further, in accordance with a preferred embodiment of the present invention, the vaccination indications are injector status indication, battery level, needle replacement, vaccine low level in each bottle, and/or number of injection for every injector.

Still further, in accordance with a preferred embodiment of the present invention, the vaccination process data includes at least one of number of injections performed, time to perform them, and temperature of the vaccine at each injection.

Moreover, in accordance with a preferred embodiment of the present invention, the process manager also includes an NFC (near field communication) unit at least to read a unique number associated with each of the injector devices.

Further, in accordance with a preferred embodiment of the present invention, each injector device also includes an RFID (radio frequency identification) reader at least to read an RFID tag associated with each the animal to be injected.

Still further, in accordance with a preferred embodiment of the present invention, each injector device also includes an anti-stabbing mechanism.

For example, in accordance with a preferred embodiment of the present invention, the anti-stabbing mechanism includes an injection head covering each needle, a switched trigger for a user to retract the injection head away from an active end of the needle, an inhibitor connected between the trigger and the injection head to move the injection head when the trigger is activated, and a locker to lock the mechanical inhibitor in a locking location when the trigger is not activated.

Moreover, in accordance with a preferred embodiment of the present invention, the switched trigger includes a mechanical trigger and at least two microswitches connected in series and indicating the movement of the trigger and the movement of the injection head.

Further, in accordance with a preferred embodiment of the present invention, each injector includes a heating element, such as a temperature controlled heating element, located at the end of a path of the at least one vaccine and/or next to the injection head.

Additionally, in accordance with a preferred embodiment of the present invention, the injector head includes a stamping pad to mark the body tissue.

Alternatively, in accordance with a preferred embodiment of the present invention, the injector includes a spray can and a marking mechanism to activate the spray can to mark the body tissue.

Further, in accordance with a preferred embodiment of the present invention, the injector head includes disinfection material.

Still further, in accordance with a preferred embodiment of the present invention, the injector head includes a pair of grabbers to grab skin over the body tissue, and a set of hinges per grabber to hold the pair of grabbers closed during a subcutaneous injection and to open the pair of grabbers otherwise.

Moreover, in accordance with a preferred embodiment of the present invention, each injector includes a projector directed towards an injection area to light up the injection area during an injection.

Further, in accordance with a preferred embodiment of the present invention, the injector head includes a connector to connect and remove the injector head from the inhibitor.

Moreover, in accordance with a preferred embodiment of the present invention, wherein a first microswitch detects contact with the mechanical trigger and a second microswitch detects contact with the body tissue.

Alternatively, in accordance with a preferred embodiment of the present invention, the system includes an injection error detection unit to detect when vaccine is flowing and the contact with the body tissue has stopped.

Further, in accordance with a preferred embodiment of the present invention, the system also includes a vibrator to vibrate while injection is still in process.

Moreover, in accordance with a preferred embodiment of the present invention, the injector also includes an injector head per needle. Each injector head includes a fixed housing, a movable housing and a protrusion limiter. The fixed housing has a connection to connect the injection head over the needle to the injector. The movable housing has an inhibitor connection to connect the movable housing to the inhibitor. The fixed and movable housings have a needle housing therein for the needle. The protrusion limiter to define how much the movable housing extends from fixed housing when the movable housing is moved by the inhibitor thereby to define the length of the needle which protrudes when injection head is retracted.

Alternatively, in accordance with a preferred embodiment of the present invention, each injector head includes a fixed housing connectable to the injector, a movable housing having a hole on a side thereof, a vaccine chamber, and a pressing unit. The vaccine chamber is connectable to vaccine pipes within the injector, the needle being connected to the vaccine chamber and aligned with the hole. The pressing unit presses the vaccine chamber to the side when the movable housing is pressed into skin of the body tissue, thereby pressing the needle through the side hole and under other portions of the skin.

Further, in accordance with a preferred embodiment of the present invention, the at least one needle is two needles and each injector includes a variable position system to vary a distance between the two needles.

Still further, in accordance with a preferred embodiment of the present invention, the database is web-accessible.

Additionally, in accordance with a preferred embodiment of the present invention, the database enables traceability of the vaccination process.

Alternatively, in accordance with a preferred embodiment of the present invention, each injector device includes a removable and retractable injection head covering each the needle.

Further, in accordance with a preferred embodiment of the present invention, each injector head includes a protrusion limiter to limit the amount the needle protrudes from the injector head.

Still further, in accordance with a preferred embodiment of the present invention, the injector also includes a multi-dosage pumping unit to receive multiple dosages of the vaccine and to inject single dosages of the vaccine per injection.

There is also provided, in accordance with a preferred embodiment of the present invention, a portable injector including at least one needle to administer a measured amount of at least one vaccine to a body tissue, an injection head covering each needle, a switched trigger for a user to retract the injection head away from an active end of the needle, an inhibitor connected between the trigger and the injection head to move the injection head when the trigger is activated and a locker to lock the mechanical inhibitor in a locking location when the trigger is not activated.

There is also provided, in accordance with a preferred embodiment of the present invention, a portable injector including at least one needle to administer a measured amount of at least one vaccine to a body tissue, and an injection head covering each needle. Each injector head includes a pair of grabbers to grab skin over the body tissue and a set of hinges per grabber to hold the pair of grabbers closed during a subcutaneous injection and to open the pair of grabbers otherwise.

There is also provided, in accordance with a preferred embodiment of the present invention, a portable injector including at least one needle to administer a measured amount of at least one vaccine to a body tissue, an injection head covering each needle. Each injector head includes a fixed housing with a connection to connect the injection head over the needle to the injector, a movable housing having an inhibitor connection to connect the movable housing to the inhibitor, and a protrusion limiter. The fixed and movable housings have a needle housing therein for the needle. The protrusion limiter defines how much the movable housing extends from the fixed housing when the movable housing is moved by the inhibitor thereby to define the length of the needle which protrudes when injection head is retracted.

There is also provided, in accordance with a preferred embodiment of the present invention, a portable injector including at least one needle to administer a measured amount of at least one vaccine to a body tissue, an injection head covering each needle. Each injector head includes a fixed housing connectable to the injector, a movable housing having a hole on a side thereof, a vaccine chamber and a pressing unit. The vaccine chamber is connectable to vaccine pipes within the injector. The needle is connected to the vaccine chamber and aligned with the hole. The pressing unit presses the vaccine chamber to the side when the movable housing is pressed into skin of the body tissue, thereby pressing the needle through the side hole and under other portions of the skin.

Finally, there is also provided, in accordance with a preferred embodiment of the present invention, a portable injector including at least one needle to administer a single dosage of at least one vaccine to a body tissue, a multi-dosage pumping unit to receive multiple dosages of the vaccine and to provide the single dosage per needle, and a heating element located after the multi-dosage pumping unit to heat the single dosage to a desired temperature.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
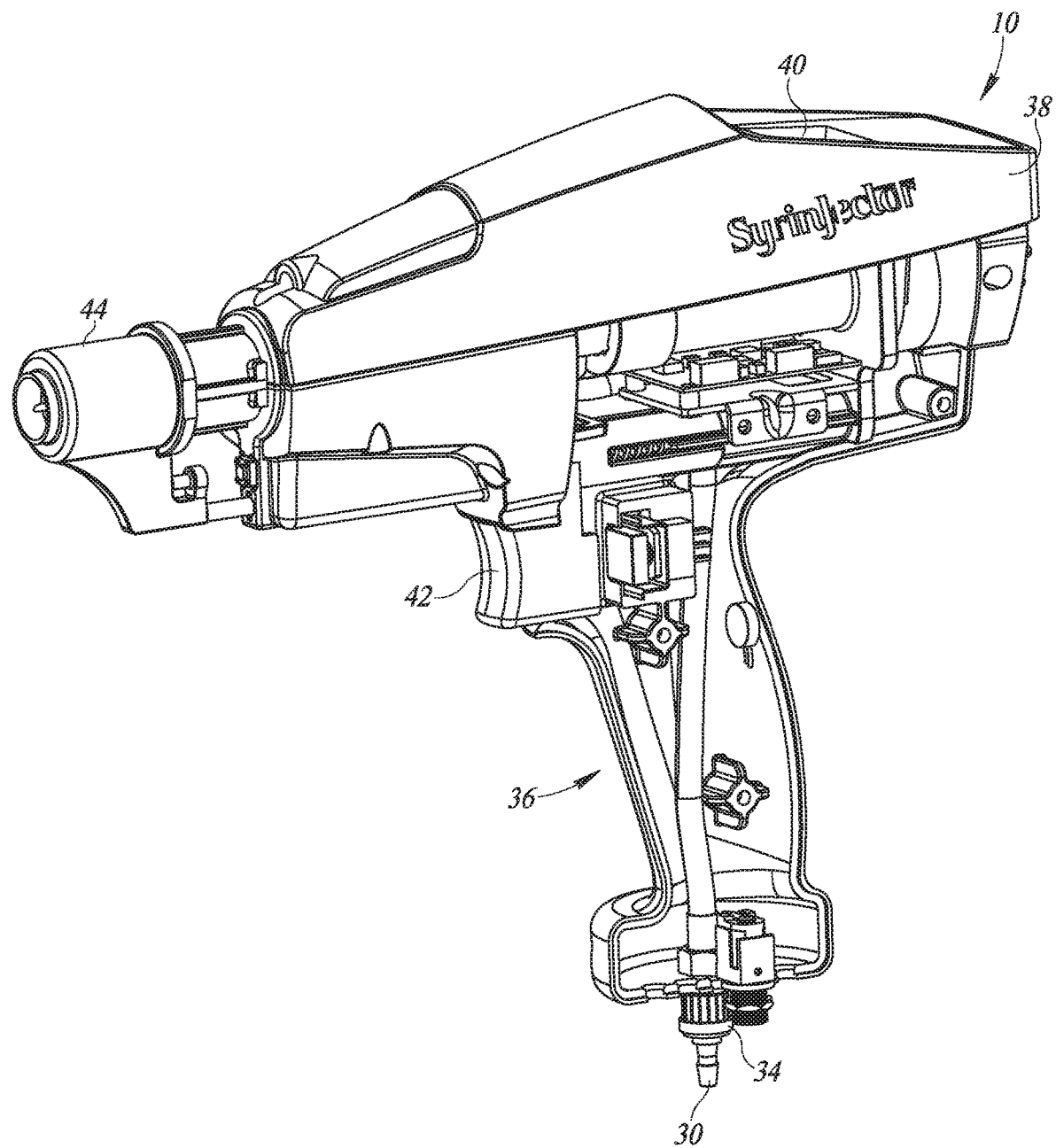
FIGS. 1A and 1B are schematic illustrations of an improved portable injector and its associated user unit, constructed and operative in accordance with a preferred embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant realized that the injector of US 2015/0174321 did not sufficiently maintain vaccine quality since the temperature at the injection point was not consistent. Moreover, while US 2015/0174321 taught an injector, it did not teach a complete solution for mass vaccination (of a herd of cattle, a brood of chicken, etc.).

Applicant realized that "biosecurity" (i.e. food sources which are reliably healthy) requires traceability about the vaccinations each animal received. This paperwork is very burdensome to the farmers but is required for modem communities to accept meat.

Applicant has also realized that it is important to keep the animals from being hurt during the injection process, which happens when injections are in the wrong place, or are too deep, or if a needle has been used for too many injections and is therefore dull. Also, when the same needle has been without disinfection between injection, it may transfer diseases in the flock or animal herd.

Figure 1B:
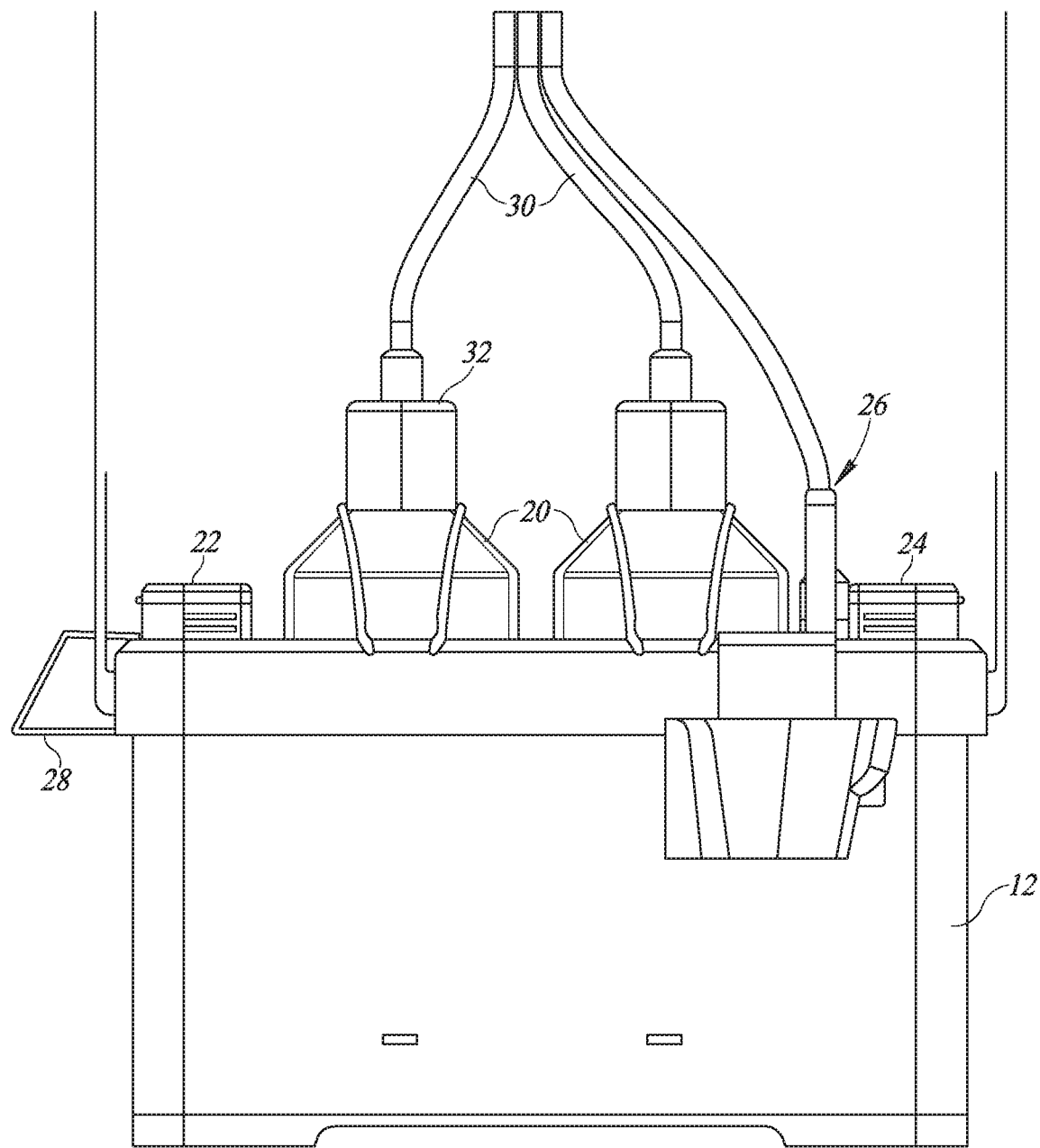
Figure 2A:
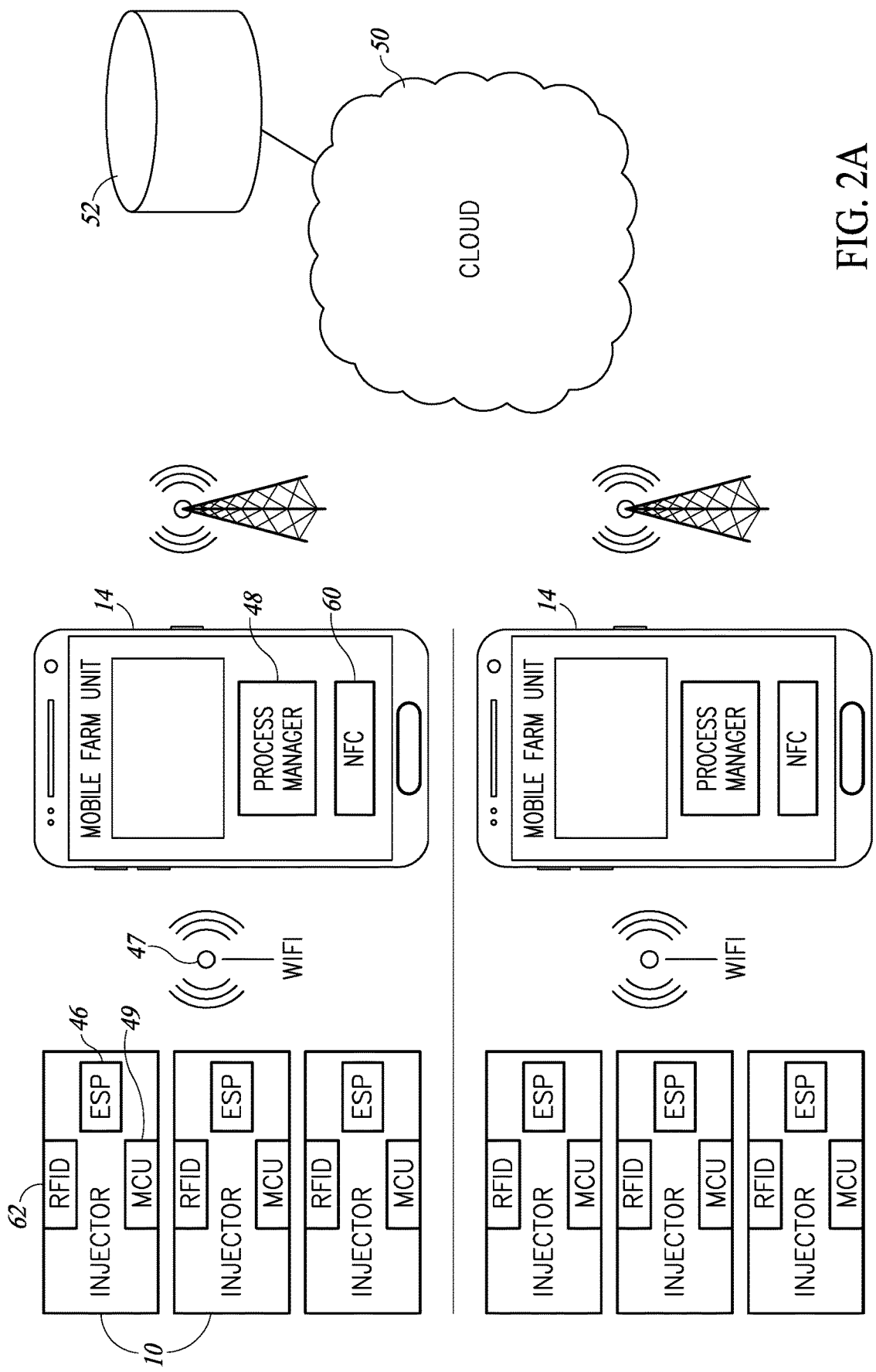
FIGS. 2A and 2B are schematic illustrations of a mass vaccination system comprising multiple injectors of FIGS. 1A and 1B, mobile farm units and an internet connected database, constructed and operative in accordance with a preferred embodiment of the present invention.
Figure 2B:
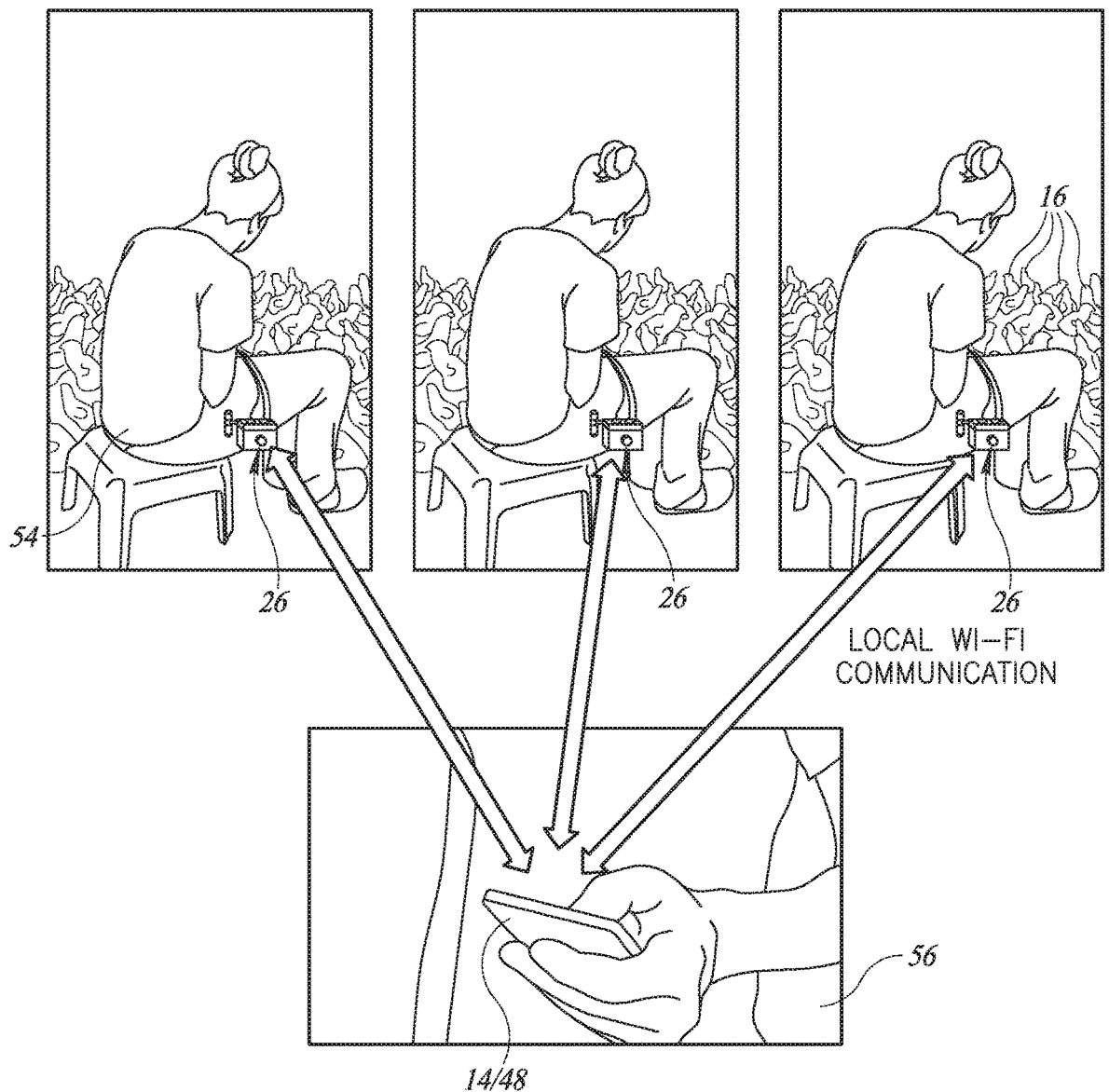

Reference is now made to FIGS. 1A and 1B, which illustrate an improved injector 10 and its associated user unit, such as a carrying bag 12, respectively, and FIGS. 2A and 2B, which illustrate multiple injectors 10 per farm communicating with a per-farm mobile unit 14 and their functioning as part of a mass vaccination of animals, such as chickens 16, respectively.

Carrying bag 12 may store multiple vaccine bottles 20, storage units 22 and 24 for new and used vaccination needles, respectively, an indicator light 26 and a brace 28 to hold its associated injector 10. Each vaccine bottle 20 may have an infusion tube 30 connected to it through its bottle cap 32. Each infusion tube 30 may end with a snap-on connection 34, to snap into the relevant location on a handle portion 36 of injector 10. Carrying bag 12 may also include a rechargeable battery and a power and voltage distribution unit.

Injector 10 may comprise handle portion 36, a pumping unit 38, a display unit 40, a trigger mechanism 42 and one or more removable and retractable injection heads 44 (FIG. 1A shows only one head). Many of its elements may be similar to those described in US 2015/0174321.

As shown in FIGS. 2A and 2B, a farm may have multiple injectors 10 to inject a significant number of animals at any one time. In accordance with a preferred embodiment of the present invention, each injector 10 may comprise an ESP unit 46, such as the ESP8266 manufactured by Espressif Systems of China, which may implement a local WI-FI 47 connection to farm unit 14. Farm unit 14 may be any mobile unit which may function outdoors where vaccinations occur. In accordance with a preferred embodiment of the present invention, farm unit 14 may be a smartphone, tablet, or a portable computerized unit with an associated process manager 48 implemented therein to operate and collect data from each mass vaccination task. For example, when, as shown in FIG. 2B, farm unit 14 is a smartphone or tablet, process manager 48 may be implemented as a mobile application.

Each farm unit 14 and process manager 48 may wirelessly communicate, such as via a cellphone connection, with the Internet 50 to upload the data collected from each mass vaccination task to an associated, web-based database 52 connected to Internet 50

Injector 10 may also function without local WI-FI communication, as described in more detail hereinbelow.

As described in more detail hereinbelow, injector 10 may also comprise a main computing unit (MCU) 49 as well as various error detection elements to detect injection errors or faults in the vaccination process by a user 54 (FIG. 2B) of injector 10 and to indicate such and other alerts to an injection process overseer 56. Whenever injector 10 may detect a fault, such as pulling out of an injection before all the vaccine has been injected, MCU 49 may instruct carrying bag 12 to activate indicator light 26 for overseer 56 to see. At the same time, MCU 49 may send a message to process manager 48 on farm unit 14 describing the error. It will be appreciated that indicator light 26 may help overseer 56 see which injector 10 is currently having a problem.

Injector 10 may also comprise a vibrator 76 (shown in FIG. 3), which may vibrate while vaccine is being injected. This may give an additional, tactile indication (in a generally noisy environment) to user 54 and may help to ensure that user 54 does not pull out early most of the time (and therefore, reducing the number of faulty injections).

As described in more detail hereinbelow, process manager 48 may also keep track of the vaccination process (injection fault, injector status indication, battery level, needle replacement, vaccine low level in each bottle, number of injection for every injector, etc.) and may activate indicator light 26 (for overseer 56 to see) any time an error exists, such as a missed vaccination, wrong amount of vaccine injected, vaccine bottle is almost empty, etc. Overseer 56 may then fix the error, if possible, or may note which user 54 or injector 10 has the most errors.

As mentioned hereinabove, ESP unit 46 may implement local WI-FI 47 between injectors 10 and process managers 48. ESP unit 46 may implement a Wi-Fi chip with a full TCP/IP stack and a main computer unit (MCU). It may support a serial Modbus or other connection from injector 10 and a wireless Modbus or other connection from process manager 48 and may have registers thereon which may be accessible by both process manager 48 (via the local WI-FI connection) and MCU 49. In one exemplary embodiment, ESP unit 46 may support the IEEE 802.11 b/g/n standard for WI-FI.

Injector 10 may also comprise an NFC (near field communication) unit 60 (FIG. 2A) and an RFID reader 62. NFC unit 60 may be any suitable NFC unit which may transmit a serial number or any other unique number relating to injector 10 to farm unit 14 when said injector 10 is placed close to farm unit 14. This may typically occur at the start of a mass vaccination task and process manager 48 may use this information to note which injectors 10 are performing the task. Typically, process manager 48 may store the serial numbers or other numbers in a memory of farm mobile unit 14 until uploading the task data to database 52.

RFID reader 62 may be any suitable RFID reader and may read the RFID tags of each animal before it is vaccinated. This is typically appropriate for herds of various kinds, where each animal is branded with an RFID tag. It is currently less appropriate for chickens which typically do not have RFID tags.

Thus, the injection task may begin with user 54 bringing injector 10 close to farm unit 14 so that the NFC unit 60 may transmit the serial number of injector 10 to process manger 48. Process manager 48 may then bring up any existing data about injector 10, such as the amount of vaccine remaining in its bottles from a previous task and/or the number of injections remaining to replace the present used needle with a new sterile one. This process may be repeated for each injector 10 to be used for this particular task.

Process manager 48 may then download the injection task parameters (vaccines to be used, dosages, etc.), typically in parallel, to the multiple injectors 10.

Then, as each animal is brought for injection, user 54 may place injector 10 near the animal's RFID tag until the animal's ID number is successfully read by injector 10. Injector 10 may communicate the animal's ID number to process manager 48 for temporary storage therein or may activate indicator light 26 if there are any errors in reading the RFID tag.

Once the injection task has finished, or at any suitable time during the injection task, process manager 48 may upload the collected data, which may comprise at least the date, the injector number, the animal number, the vaccine information and any error information, to database 52.

As mentioned hereinabove, injector 10 may also function without local WI-FI communication. As described in more detail with respect to FIG. 3, for this, injector 10 may include a man machine interface (MMI) comprising LCD display unit 40, keyboard 89 (not shown) and status indicators 87 (not shown), all controlled by MCU 49. Status indicators 87 may comprise a multiplicity of LEDs.

While Wi-Fi communication is not operative, some injection data may be entered via keyboard 89, NFC unit 60 and RFID reader 62. The rest may be generated by injector 10 and all the data may be saved in the memory of MCU 49. When Wi-Fi communication may be restored, all saved injection data may be transmitted to farm unit 14 which, at the end of injection process, may transmit the data to database 52.

It will be appreciated that the present invention may enable injectors 10 to communicate, in real-time, with process manager 48 within the farm mobile unit 14 for real-time data collection about the injection process. This real-time data collection of the vaccination may allow traceability of the vaccination process and it eases paperwork. Database 52 may be web-accessible to all those involved in the vaccination process, such as the farmers, veterinarians, buyers of the meat, insurance companies who may insure the farmers and bankers who may support the farmers. In addition, the data in database 52 may be accessible for post injection process control by any suitable application which may provide information necessary to improve the decision making and/or for improving injection processes. For example, post process control may involve determining the number of injections per mass vaccination, average number of injections per hour, average temperature of the vaccination at the time of vaccination and various other statistics.

Figure 3:
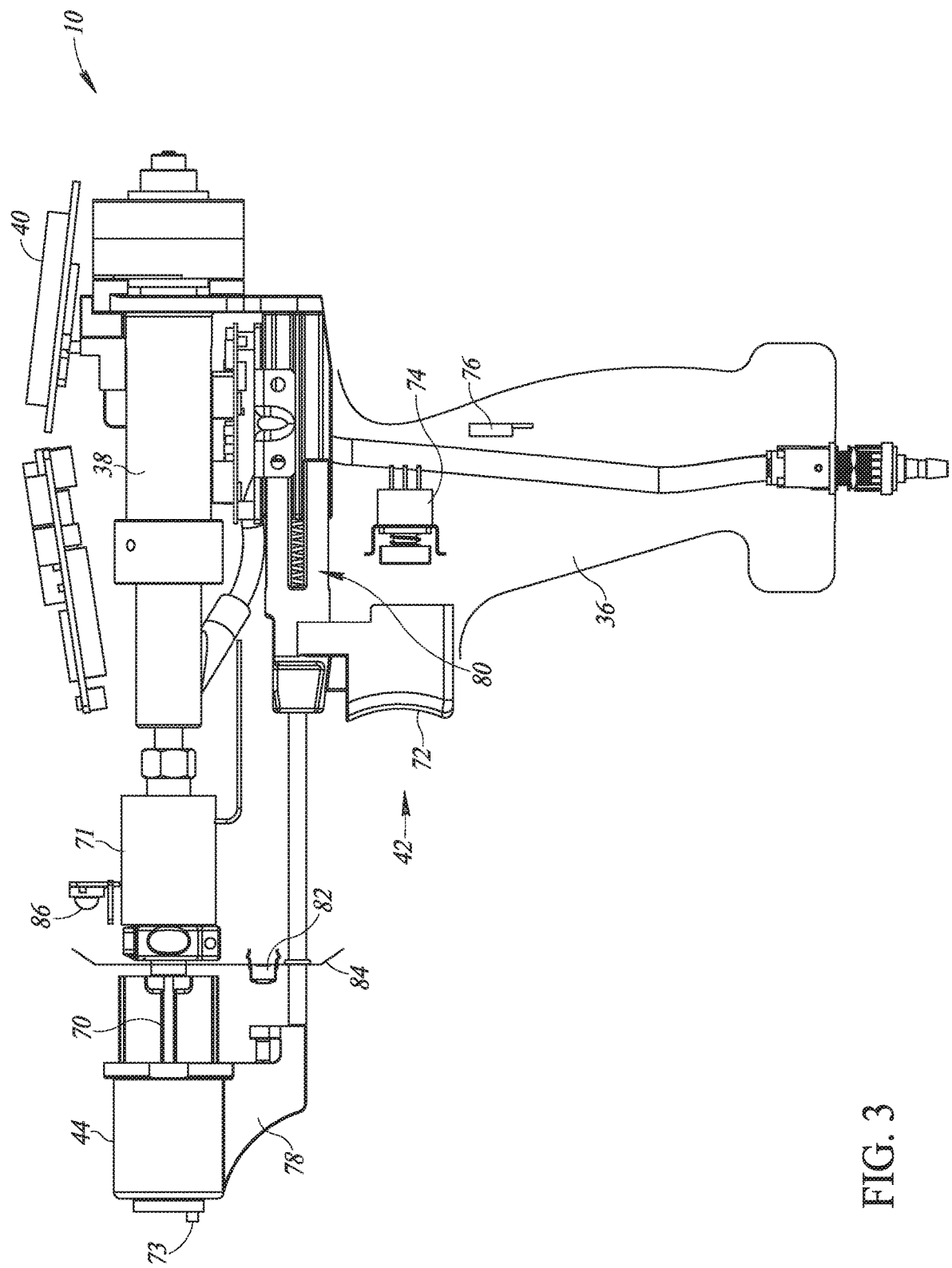
FIG. 3 is a detailed illustration of the elements of the portable injector of FIG. 1A.
Figure 4:
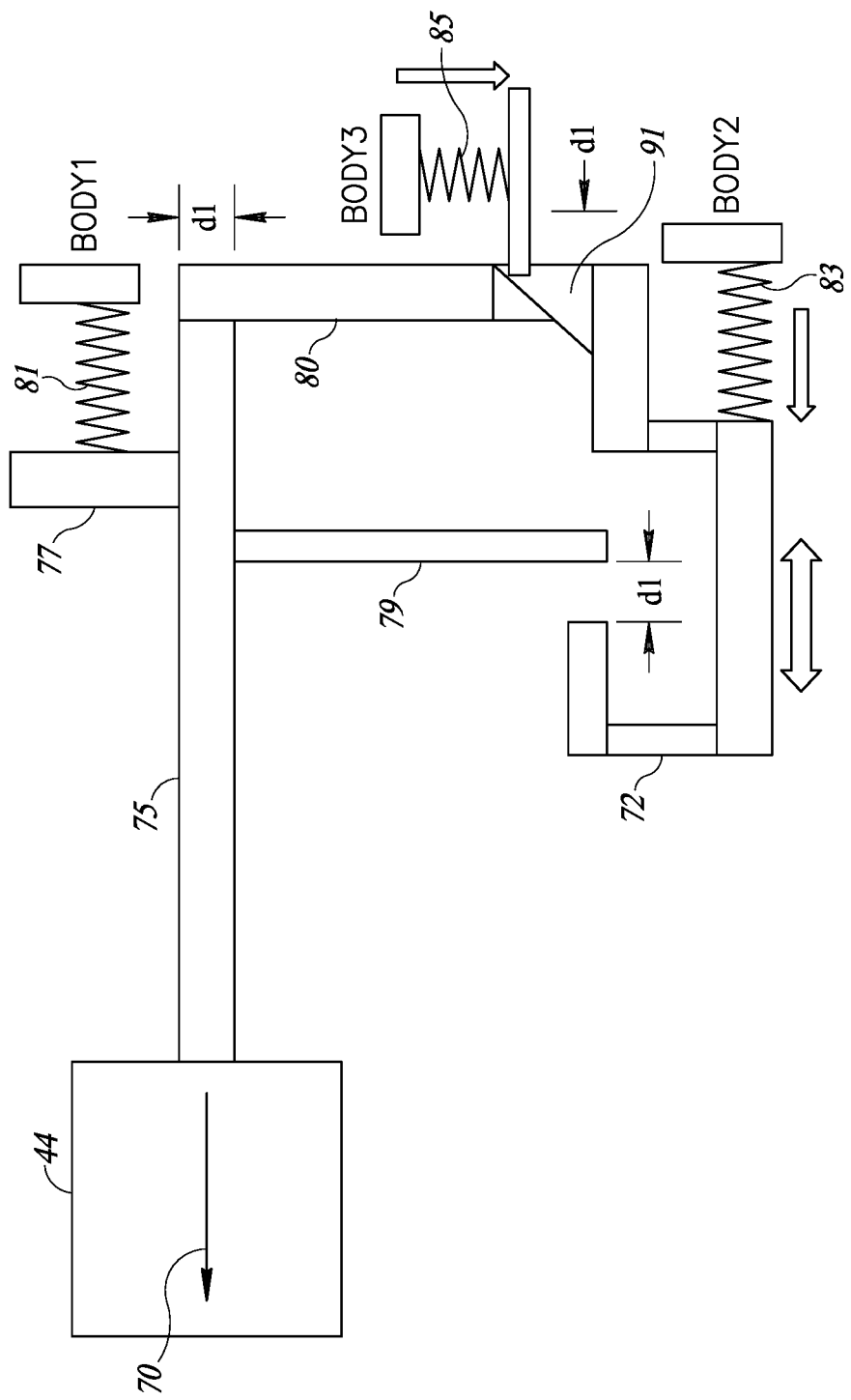
FIG. 4 is a schematic illustration of the elements of the portable injector of FIG. 1A which implement an anti-stabbing mechanism.

Reference is now made to FIG. 3, which illustrates the mechanical elements of one embodiment of injector 10 and to FIG. 4, which details an anti-stabbing operation of injector 10. As mentioned hereinabove, the main elements of injector 10 are handle portion 36, pumping unit 38, display unit 40, trigger mechanism 42 and a removable and retractable injection head 44 covering a needle 70. Injector 10 may also comprise a vaccine heater unit 71 near needle 70.

Trigger mechanism 42 comprises a trigger 72, a safety microswitch 74 and a vibrator 76. Trigger 72 may be integrally connected, via a mechanical inhibitor 75, to a retraction unit 78 into which injection head 44 may be connected and to a locker 80 which may lock mechanical inhibitor 75 when trigger 72 is not pressed, thereby keeping injection head 44 from retracting. As a result, the needle 70 is not exposed, except when injection occurs (this is an anti-stabbing mechanism).

When user 54 pushes trigger 72, trigger 72 will close safety microswitch 74 and will pull retraction unit 78 towards vaccine heater unit 71. This will expose needle 70 enough for an injection. As will be explained hereinbelow, the amount of retraction is controllable.

In addition, injector 10 may have a contact microswitch 82 on its surface 84 facing injection head 44. Contact switch 82 may be activated when injection head 44 may touch surface 84.

It will be appreciated that electrically, injection microswitch 74 and contact switch 82 may be connected in series such that no vaccine may be injected until both switches are closed. Since inhibitor 75 may not move unless trigger 72 is pressed, injection head 44 may provide an anti-stabbing mechanism.

Referring to FIG. 4, the anti-stabbing operation may be achieved as follows. Inhibitor 75 may comprise a horizontal rod, labeled 75, an upper vertical rod 77 and a lower vertical rod 79. At stand still, when trigger 72 is not pressed, horizontal rod 75 may be blocked from movement by locker 80, which is shown in FIG. 4 as a vertical rod. Locker 80 may prevent injection head 44 from moving in any direction. This may maintain needle 70 covered. In this state, injector 10 may be locked in the anti-stabbing mode.

A mechanical unit 91, may be part of trigger 72, may conform to a triangular end shape of locker 80 and may hold locker 80 in place, which, in turn, may disable inhibitor 75 from moving in case injection head 44 is pressed by mistake. When user 54 may press trigger 72 to the right, trigger 72 may travel a distance dl until it touches lower rod 79. The movement of trigger 72 may move mechanical unit 91 a distance dl away from locker 80 which, in turn, may lower locker 80 down a predetermined distance, such as distance dl. As a result, locker 80 may no longer lock the motion of inhibitor 75.

With inhibitor 75 no longer locked in place, further pressing on trigger 72 may push lower vertical element 79 to the right, thereby pulling injector head 44 to the right and exposing needle 70 for injection. When user 54 may press injection head 44 against the body of an animal or human, injection head 44 may move more to the right, causing contact microswitches 82 to be closed and exposing needle 70 the full amount for injection.

When user 54 no longer presses on trigger 72, three springs 81, 83 and 85 may return all elements to their stand still positions. Spring 81 may press between upper vertical rod 77 and a portion of the housing of injector 10 (labeled 'body1') to return horizontal rod 75. Spring 83 may operate between trigger 72 and a second portion of the housing (labeled 'body2') to return trigger 72. Spring 85 may press between upper vertical rod 77 and a third portion of the housing (labeled 'body3') to return locker 80 to its upper locking position.

Injection head 44 may also comprise a contact microswitch 73 at the farthest end thereof from surface 84. Surface 84 may, alternatively, be a longer rod of metal or any other material. This may enable user 54 to give the injection a small distance away from the animal body, such as when injecting a wild animal and/or beef cows in pasture. Contact microswitch 73 may detect contact with the skin of the animal to be vaccinated. Its signals may be provided to MCU 49 through contact microswitches 82 and 74. These 3 switches may be connected in series.

Moreover, if contact microswitch 73 is active when either of switches 74 and 82 are not closed, then MCU 49 may ensure that no vaccination occurs, as this indicates contact with a body other than during an injection process. Since MCU 49 may only activate injection when all three switches 74, 82 and 73 are closed, this may provide self-injection protection.

Once both switches 74 and 82 are closed, MCU 49 may activate pumping unit 38 and vibrator 76 and may keep them activated for a predetermined amount of time related to the vaccine dosage or until one of the switches 74 or 82 opens. Thus, if either switch 74 or 82 opens before the predetermined time has ended (such as when a pumping piston (shown in FIG. 12 hereinbelow) pushing the vaccine towards needle 70 didn't reach its endpoint when the entire vaccine dosage has been transferred), MCU 49 may detect an error and may, in response, activate indicator light 26 in the carrying bag 12 and a red light near display unit 40, and transmit an error notification to process manager 48.

It will be appreciated that vibrator 76 may stop when either of switches 74 or 82 opens. This may provide a tactile indication to user 54 of a problem with the vaccination process.

Spring 83 may return trigger 72 to its original position once user 54 stops pressing trigger 72. In an alternative embodiment, trigger mechanism 42 may also comprises an optical sensor to sense the return of trigger 72 to its original position. If the return is incomplete, MCU 49 may detect an error and may provide the relevant alerts.

In accordance with a preferred embodiment of the present invention, vaccine heater 71, such as a heating element, may be located at the end of path of the vaccine, just before the vaccine enters needle 70. This may provide temperature controlled heating, set to the appropriate temperature for the vaccine dose being injected, just before injection. It will be appreciated that this may ensure that the temperature of the vaccine is generally ideal for the injection process and may enable the vaccine to flow more consistently. It may also make the vaccination a more pleasant one for the animal as well as maximize the functioning of the vaccine within the body of the animal.

In accordance with a preferred embodiment of the present invention, injector 10 may also comprise an LED projector 86 connected to the upper portion of vaccine heater 71. LED projector 86 may be angled to highlight the injection point, making the injection location more visible to user 54 and making it possible to work in difficult lighting situations as are common on farms. LED projector 86 may be activated and controlled by MCU 49.

Figure 5:
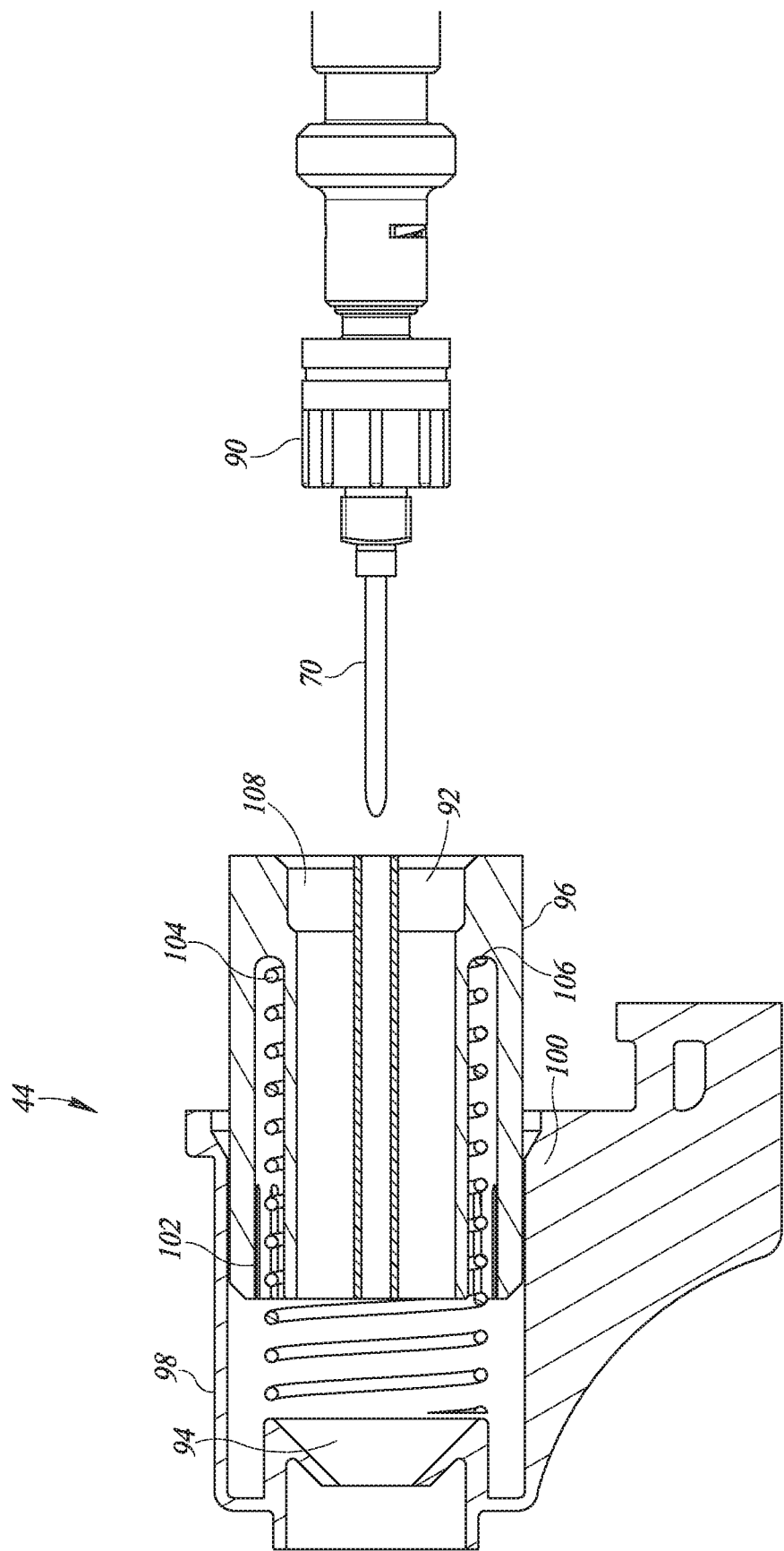
FIG. 5 is a detailed illustration of an injection head and a needle, forming part of the portable injector of FIG. 1A.

Reference is now made to FIG. 5, which details needle 70 and injection head 44. Needle 70 may be removably connected to a base 90 designed to allow vaccine liquids to flow therethrough.

Injection head 44 may comprise a flexible housing 92 within which needle 70 may be held. Injection head 44 may also comprise disinfection material 94, shown located at a distal end of injection head 44 such that, when injection head 44 is retracted and returned, needle 70 may pass back and forth through disinfection material 94. Injection head 44 may also comprise a fixed housing 96 and a movable housing 98 as well as an inhibitor connection 100 forming part of movable housing 98 to connect movable housing 98 to inhibitor 75. Both of fixed housing 96 and movable housing 98 have a needle housing to hold needle 70.

A rotating screw 102, which may turn on a screwed surface outside flexible housing 92, may change how much movable housing 98 extends from fixed housing 96 and thus, may define the length of needle 70 which may protrude when injection head 44 may be retracted. This may define the depth of the injection, which may be different for intramuscular and subcutaneous injections, and it may be changed by millimeters.

Fixed housing 96 may include a springed bayonet connection 108 by which user 54 may connect injection head 44 over needle 70 to base 90 on the far end of injector 10. For this spring 104 may be held between a lower surface 106 of fixed housing 96 and rotating screw 102. It will be appreciated that user 54 may remove injection head 44 each time s/he needs to change needle 70 and that bayonet connection 108 may provide a quick attachment mechanism for easy removal and replacement of needles 70.

Disinfection material 94 may be any suitable material which will hold a disinfecting liquid as well as act as a towel to remove the liquid when needle 70 passes through it. Disinfection liquid may be formed of 2.5% Glutaraldehyde and 5% Bardac 22 (Didecyl Dimethyl Ammonium Chloride).

Figure 6B:
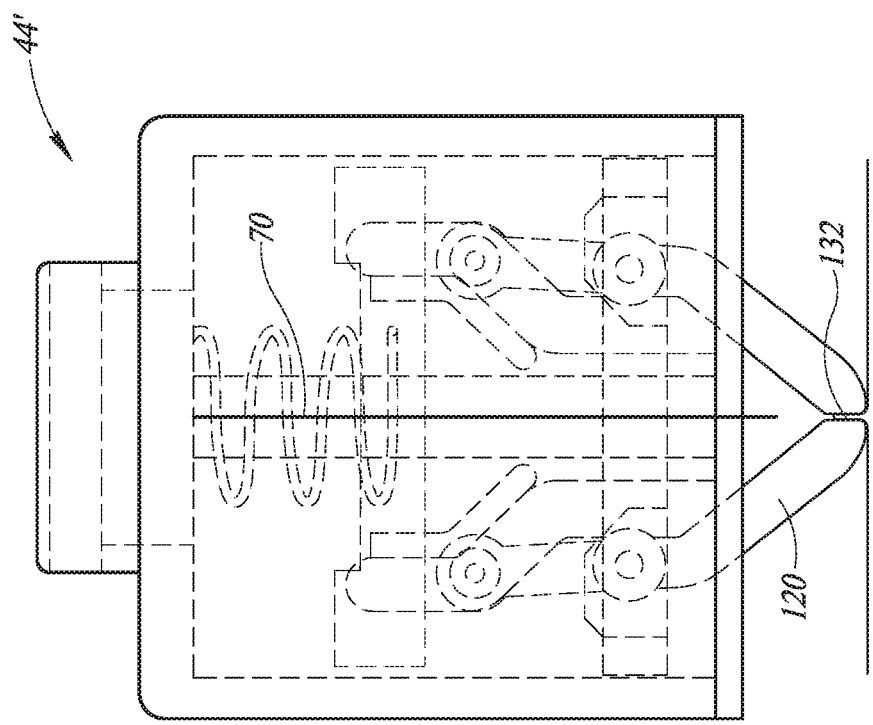
FIGS. 6A and 6B are detailed illustrations of an alternative injection head in an open and a closed position, respectively, useful for subcutaneous injections.
Figure 6A:
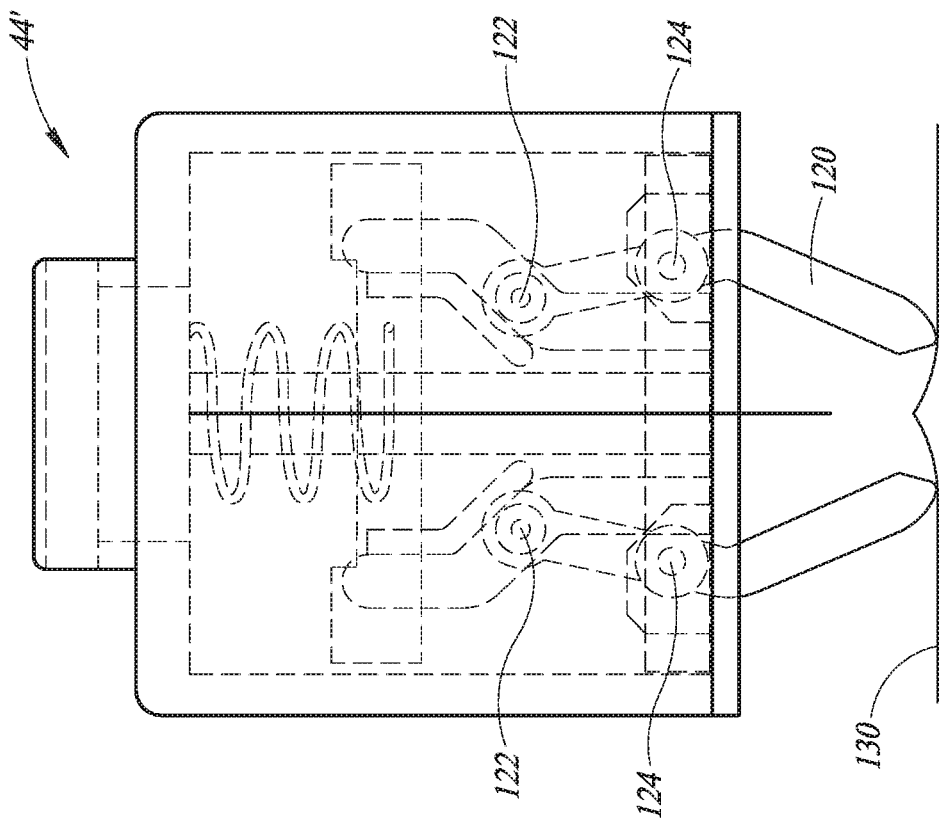

Reference is now made to FIGS. 6A and 6B, which illustrates an alternative embodiment of injection head 44, labeled 44', having a pair of grabbers 120 to aid in subcutaneous injections. FIG. 6A illustrates injection head 44' with grabbers 120 in an open position while FIG. 6B illustrates injection head 44' with grabbers 120 in a closed position.

Injection head 44' may comprise hinges 122 and 124 per grabber which may straighten out when injection head 44' is pressed against skin 130 and retraction unit 78 retracts upper housing 98. The straightening of hinges 122 and 124 may cause grabbers 120 to close on and lift a portion 132 of skin 130 away from the body while that upper housing 98 of injection head 44' is being retracted. Needle 70 may then protrude right into portion 132 for subcutaneous injection.

Figure 7A:
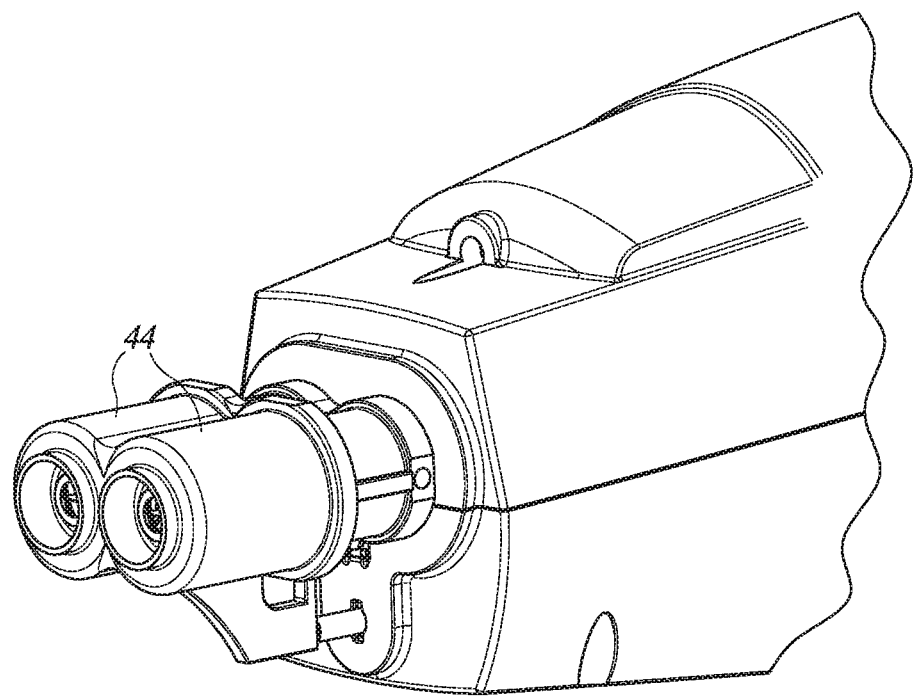
FIG. 7A is a schematic illustration of an alternative injector having two injection heads.
Figure 7B:
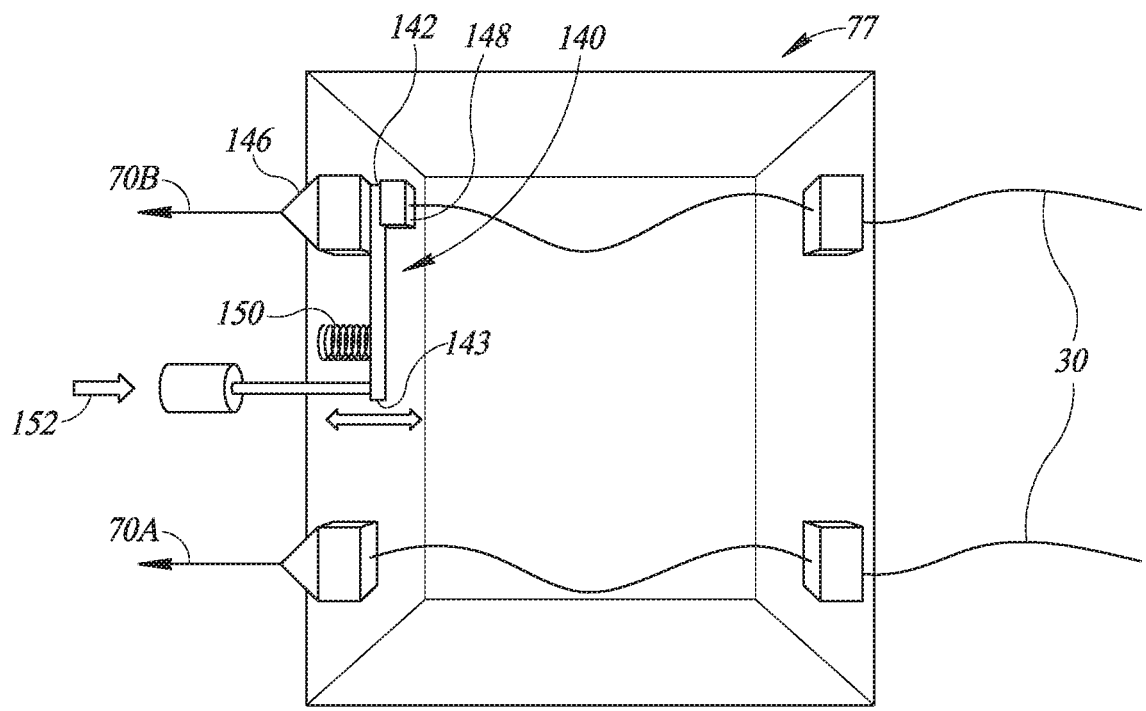
FIGS. 7B and 7C are schematic illustrations of a variable position system for the needles operating with the two injection heads of FIG. 7A.
Figure 7C:
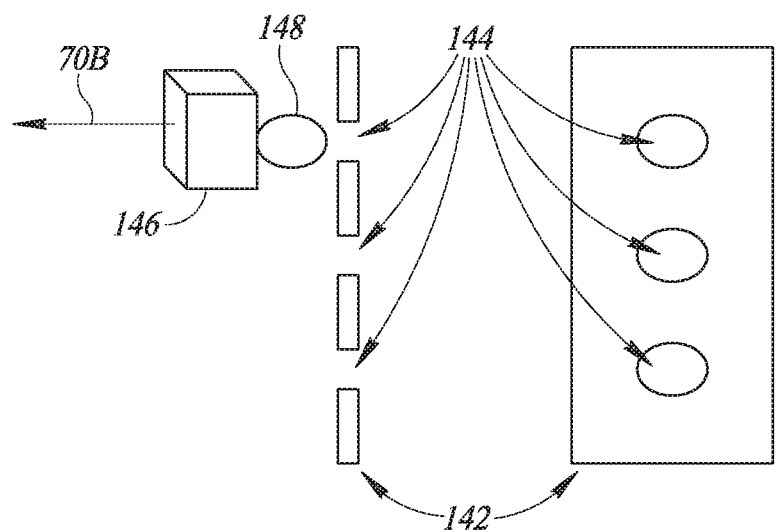

Reference is now made to FIG. 7A which illustrates an alternative embodiment of injector 10 having two injection heads 44, each injecting a different vaccine at generally the same time. Reference is also made to FIGS. 7B and 7C, which schematically illustrate a variable position system 140 which allows user 54 to vary the distance between needles 70 of the two injection heads 44. This may be particularly useful when injecting poultry where the injection area for some of the poultry is very small and caution is needed to avoid injection into the poultry bone.

As shown in FIG. 7B, injector 10 may hold both needles 70, here labeled 70A and 70B, in two locations, each receiving vaccine via different infusion tubes 30. One of the needles, for example, needle 70A, may be fixed, while the other needle, 70B, may be located within variable position system 140. System 140 may comprise a plate 142 with a multiplicity of holes 144, a slider 146 to which a metal ball 148 may be attached, a spring 150, and a button press 152.

When user 54 may push button press 152, button press 152 may press against a loose end 143 of plate 142, releasing ball 148 from its current hole 144. Slider 146 may then be moved to a different hole 144. When button press 152 is released, spring 150 may return plate 142 to its location, thereby maintaining ball 148 in its current hole 144.

Figure 8A:
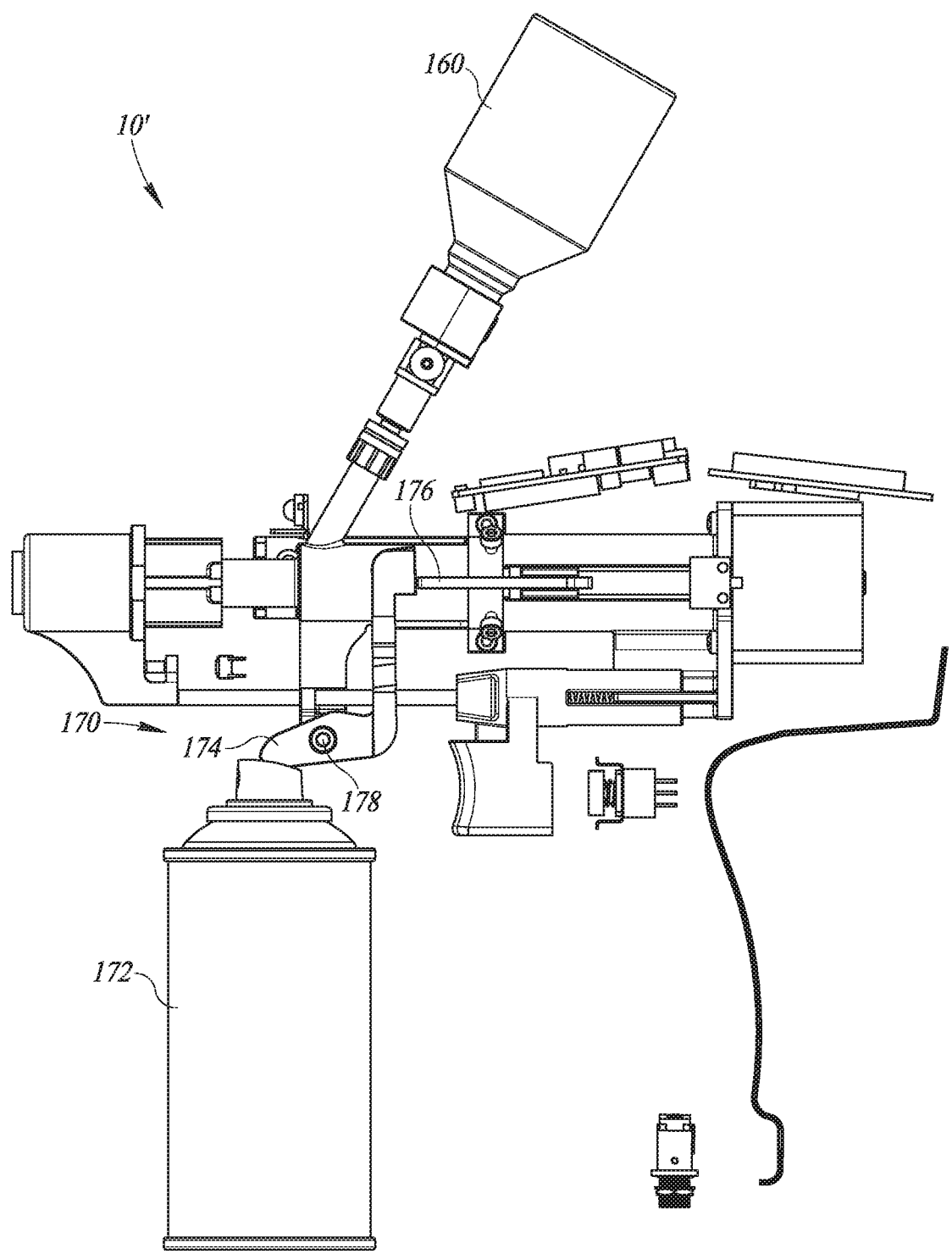
FIGS. 8A and 8B are schematic illustrations of an alternative injector having a color spraying unit.
Figure 8B:
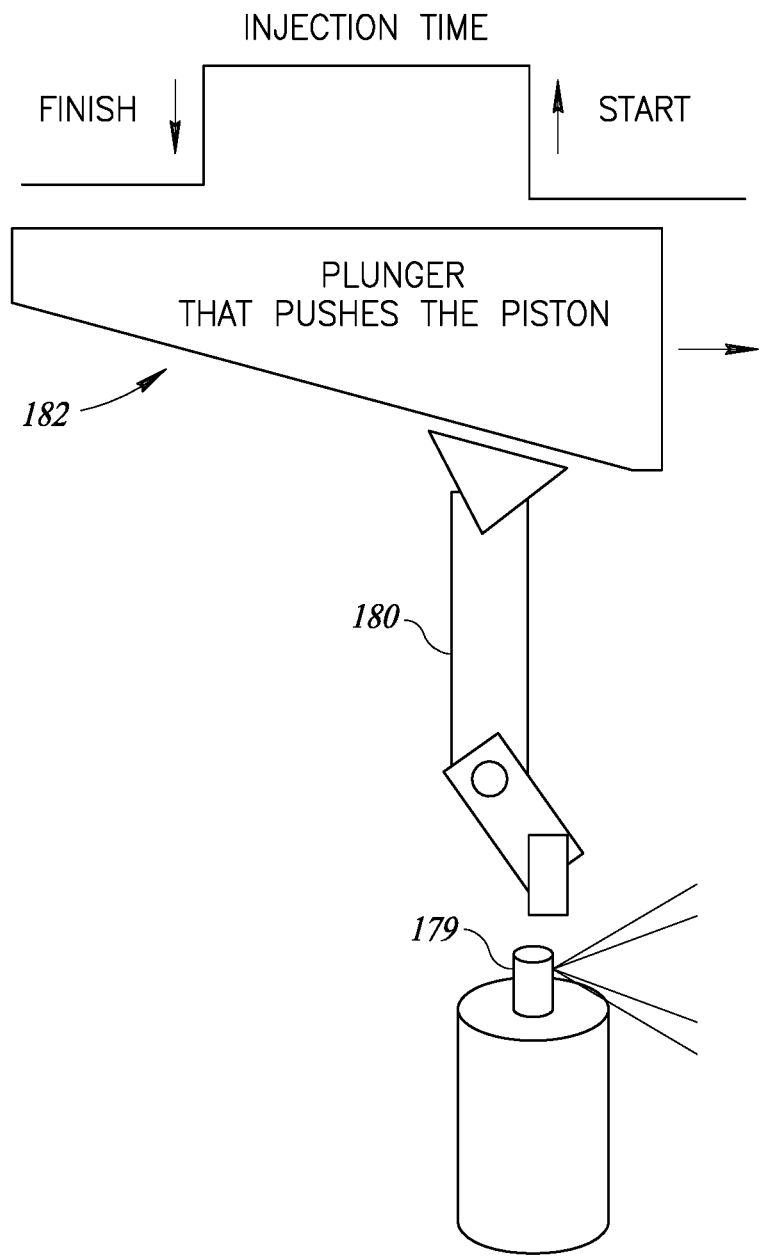

Reference is now made to FIGS. 8A and 8B, which illustrate an alternative embodiment of the present invention. FIG. 8A illustrates an injector 10' designed for pigs and other animals which receive vaccine stored in smaller bottles 160. In this embodiment, smaller vaccine bottles 160 may be connected directly to injector 10', rather than via infusion tubes 30. Typically, injector 10' may still be operated with carrying bag 12 or something similar, to both hold other bottles of vaccine and to provide indicator light 26.

FIG. 8A also shows a marking mechanism 170 to mark already vaccinated animals. For example, marking mechanism 170 may comprise a color spray bottle 172 that may be activated to spray a spot of paint onto the skin of the animal being vaccinated at the end of an injection. It will be appreciated that such a marking may make it relatively simple to determine which animals of a large, milling herd still need to be vaccinated.

Marking mechanism 170 may also comprise a rocker 174 pushable by a piston 176 which may be activated by MCU 49 towards the end of an injection period. Rocker 174 may be connected to the frame of injector 10' and may rotate around an axis 178, pressing down on a sprayer 179 of color spray bottle 172.

FIG. 8B illustrates an alternative embodiment of marking mechanism 170. In this embodiment, mechanical inhibitor 75 may have a diagonal shape near color spray bottle 172 and may press on a hinged mechanism 180 which, in turn, may touch or come close to sprayer 179. As mechanical inhibitor 75 may move to the right during the injection period (noted in FIG. 8B by the graph labeled "Injection Time"), hinged mechanism 180 may slowly straighten out such that, at the point labeled 182, it may be fully extended and may, at this point, press hard on sprayer 179, releasing color from color spray bottle 172.

Figure 8C:
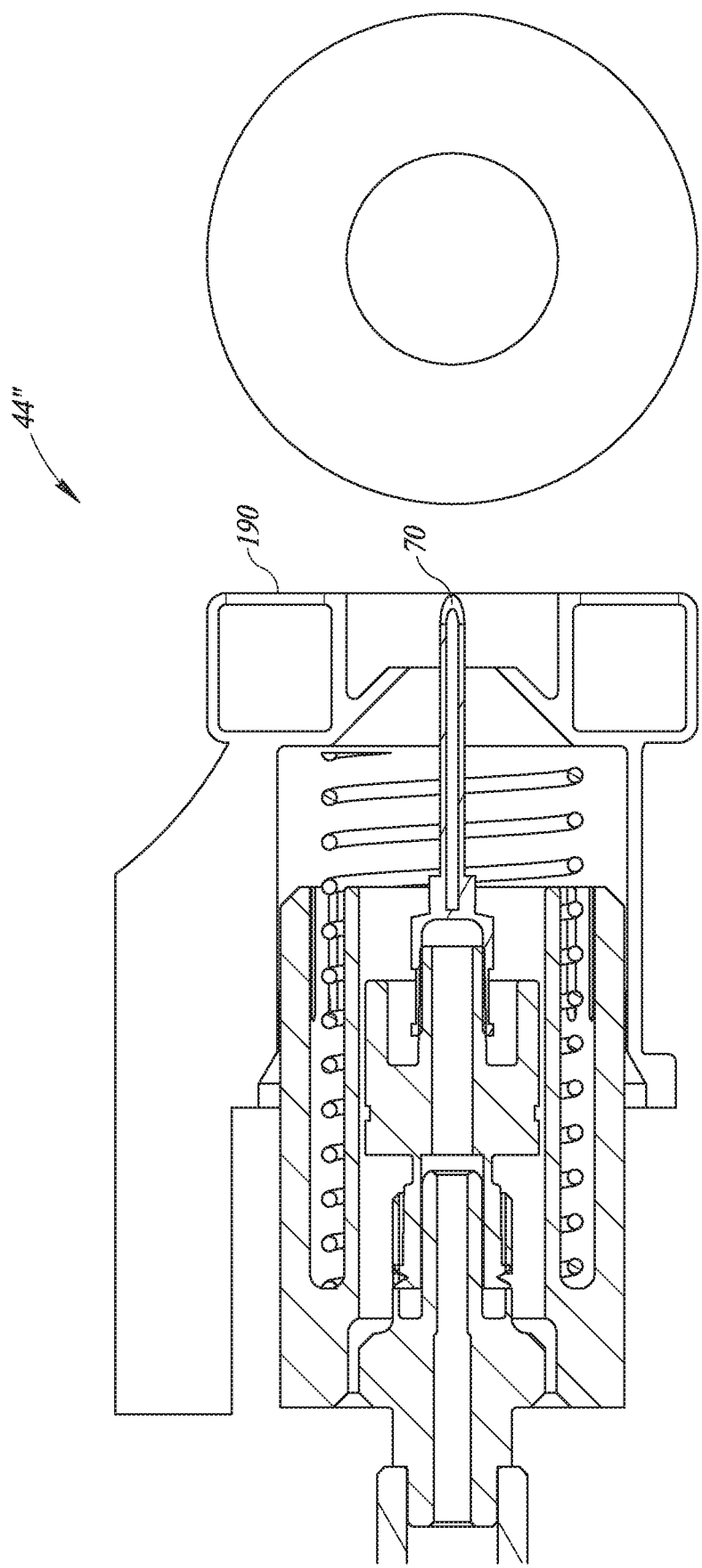
FIG. 8C is a schematic illustration of an alternative injection head having a color stamping unit.

Reference is now made to FIG. 8C, which illustrates an alternative marking method. In this embodiment, injection head, here labeled 44", may comprise a ringed stamper 190 at its end thereof. Ringed stamper 190 may be formed as a ring around needle 70 and may store a ringed pad of die. When injection head 44' may be pressed against the skin of the animal during the injection process, stamper 190 may stamp die onto the skin, around the injection area.

Figure 9:
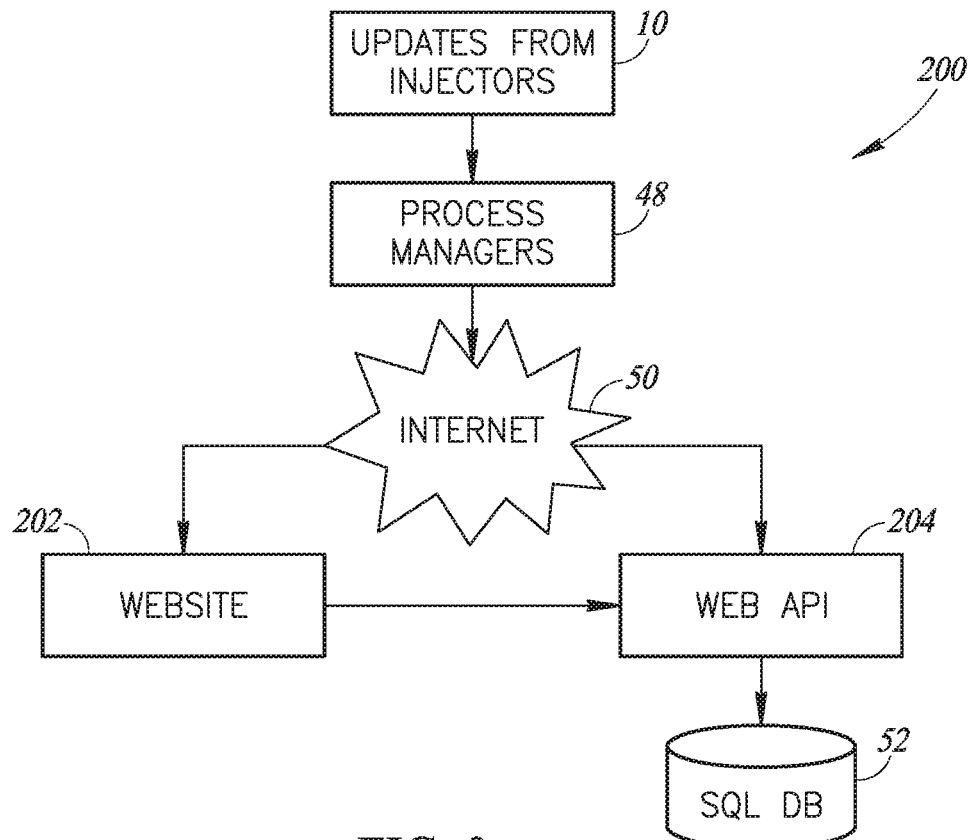
FIG. 9 is a schematic illustration of the system architecture of the online, real-time mass vaccination system of the present invention.

Reference is now made to FIG. 9, which illustrates the system architecture of the online, real-time, mass vaccination system, here labeled 200, of the present invention. As discussed hereinabove, system 200 may keep track of each mass vaccination task and may also keep track of errors and notifications. Microswitches 73, 74 and 82 indicate when a vaccination is happening (data which system 200 may store) and may also notify MCU 49 when a vaccination is incomplete, as described hereinabove. As mentioned hereinabove, MCU 49 may provide an error indication via indicator light 26, vibrator 76 and may notify processor manager 48.

System 200 may also comprise other sensors to sense battery voltage levels, temperature of vaccine, etc. Sensors for the quality of the vaccine are discussed in U.S. Patent Publication Ser. No. 2015/0174321, incorporated herein by reference.

In addition, process managers 48 may keep track of the start and stop of each vaccination and from these may determine at least the following:

When to replace needles (per count of injections);

When a vaccine bottle 20 may be about to run out of vaccine (based on number of injections, known amount being injected each time and known volume of tubing from bottle to needle);

Number of injections for every injector (per count of injections);

Faulty injections per each injector;

When to replace disinfection unit;

When to replace stamping pad;

When to replace color spray bottle; and

When to replace or recharge the battery.

Process managers 48 may also keep track of the number of errors which injectors 10 may generate as well as the number of errors each user 54 may generate.

Process managers 48 may upload the data collected for each mass vaccination task during or after the task, via Internet 50 to database 52. System 200 may also comprise a website 202 which may present the information from database 52, typically accessed via a web API (application programming interface) 204.

In operation, when a mass injection task has begun, the relevant process manager 48 may receive injection task definition data from overseer 56 and may store it into a local database (partial mirror) within process manager 48 so the mass injection task may operate independently if the connection to internet 50 is down.

The relevant process manager 48 may declare itself as a WI-FI access point for its associated injectors 10 and may communicate with its associated injectors 10 via each ESP 46 (FIG. 2A) by reading from and writing to the relevant registers of each ESP 46.

Figure 10:
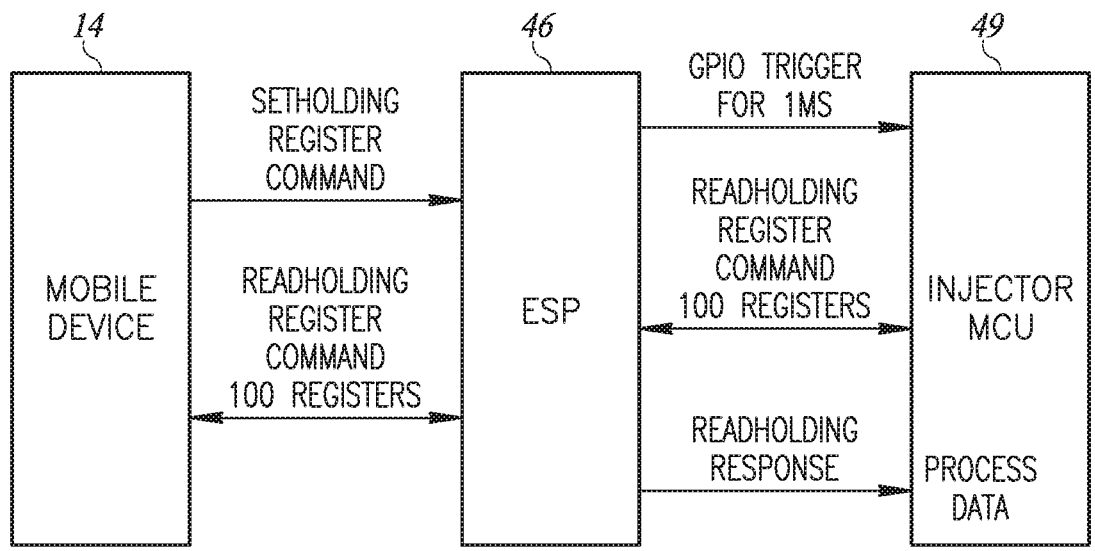
FIG. 10 is a schematic illustration of the data flow between one mobile farm unit and one injector of FIG. 2A.

Reference is now briefly made to FIG. 10, which illustrates the data flow between mobile device 14, ESP 46 and MCU 49. Mobile device 14 may send a Set Holding register command to ESP 46 to ask for data from injector 10. ESP 46 may, in turn, trigger an I/O port on MCU 49 for a predefined length of time, such as 1ms, thereby to request MCU 49 to upload data to ESP 46. In response, MCU 49 may upload data (a Read Holding command) to the relevant registers, based on which I/O port was triggered. For example, MCU 49 may upload data to 100 registers. Once ESP 46 has received the uploaded data, ESP 46 may respond to mobile device 14 with the data received in response to the Read Holding command. After reading the relevant registers, process manager 48 may send the data it has collected (tasks, injector state, etc.) to database 52. For example, the data to be stored for post processing might be:

Injector ID—from NFC communication;

Animal ID—from RFID communication;

Vaccine bottle ID—entered into process manager 48;

Status of injection—from injector operation;

Farm ID—from process manager 48; and

Other information

Process manager 48 may control the mass vaccination process. Process manager may have a page or screen that may provide a list of injectors and their statuses (on, off, rest, error). Process manager 48 may enable overseer 56 to create a task, by defining injection parameters for the entire injection process, or to stop an existing task. These injection parameters may be downloaded to the injectors 10 which have been registered for the task, typically via local WI-FI communication.

If a task is currently running, overseer 56 may click on a listed injector and may view data which have been received from the injector, as well as its statistics. If the task has finished, process manager 48 may display a message. If process manager 48 may receive an error message from an injector 10, process manager 48 may display a notification and may generate a short vibration of mobile device 14.

Figure 11:
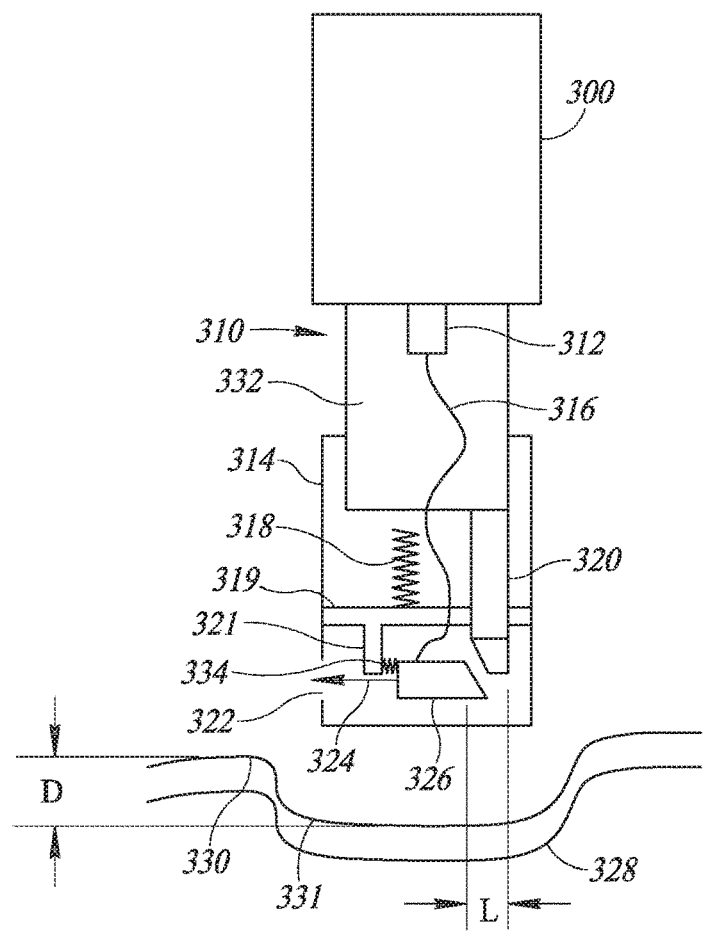
FIG. 11 is a schematic illustration of alternative injection head, useful for subcutaneous injections.

Reference is now made to FIG. 11, which illustrates an alternative embodiment, labeled 310, of the injection head, also useful for subcutaneous injection. In this embodiment, injection head 310 is mechanically connected, as described hereinabove, to the injector, here shown schematically as injector 300.

Subcutaneous injection head 310 comprises a vaccine pipe 316, connectable to injector 300 via a connection 312, a fixed housing 332, a movable housing 314, a spring 318 connected to a frame 319 of moveable housing 314, a pressing unit 320, a vaccine chamber 326, a needle 324 connected to said vaccine chamber and a small hole 322 on the side of movable housing 314 to which needle 324 is aligned. Frame 319 may also include a rod 321 extending below it, near vaccine chamber 326. A spring 334 may extend between rod 321 and vaccine chamber 326 and may press vaccine chamber 326 to the right at stand still.

User 54 may press subcutaneous injection head 310 into skin 330 to a depth of D mm, which may press movable housing 314 towards fixed housing 332 and may, after D mm, begin to press spring 318. After D mm, pressing unit 320, which may have a triangular-shaped end, may be moved down and may push vaccine chamber 326 and needle 324 against spring 334 a distance L to the left, though hole 322. Since movable housing 314 has pressed into skin 330 and since needle 324 may issue from subcutaneous injection head 310 on the side of head 310, needle 324 may enter skin 330 at a point, such as point 331, which is on the side of injection head 310 but under the upper surface of a different portion of skin 330 (i.e. subcutaneously).

When user 54 may pull injection head 310 away from skin 330, spring 324 may return vaccine chamber 326 to the right. As user 54 may continue to pull injection head 310 away from skin 330, spring 318 may return housing 314 to its stand still location.

Figure 12:
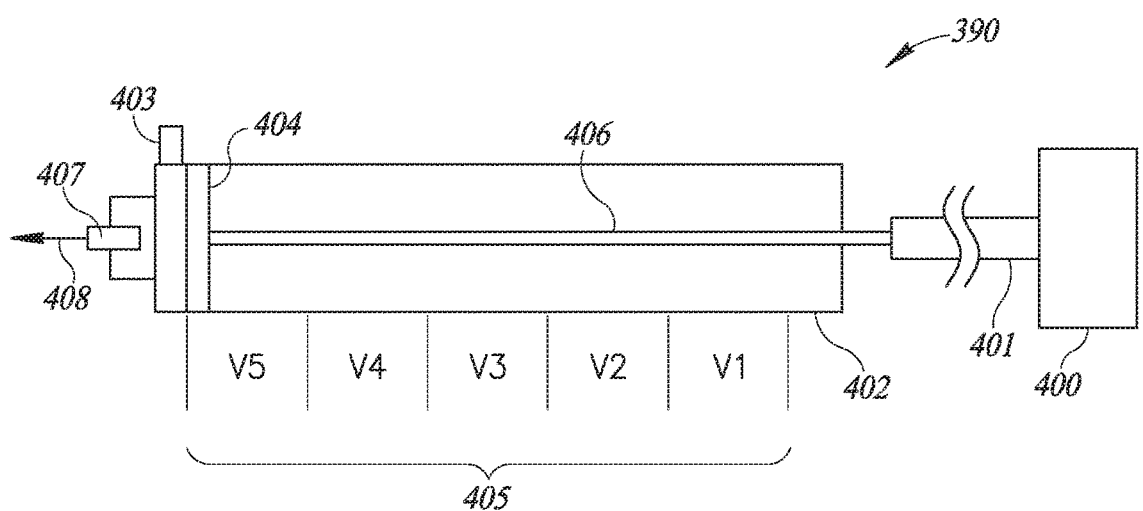
FIG. 12 is a schematic illustration of an improved vaccine pumping system, forming part of the injectors of FIGS. 1A and 7A.

Reference is now made to FIG. 12, which illustrates a multi-dosage pumping unit 390, forming part of injectors 10 or 10', which may reduce battery consumption and wear of the pumping system. The vaccine pumping system may comprise a stepper motor 400, a chamber 402 with a piston 404 moving therein, an intake valve 403 and an exit valve 407.

In accordance with a preferred embodiment of the present invention, chamber 402 may be large, such that unit 390 may pull multiple dosages Vi of vaccine into chamber 402 at one time while injecting only one dosage at a time. Since the process of pulling vaccine into chamber 402 is both power consuming and mechanically wearing while the process of pushing the vaccine out of chamber 402 is not, reducing the number of times it is performed saves power and wear and tear.

Under instructions from MCU 49, stepper motor 400 may rotate a screw 401 which may be connected to a rod 406 forming part of piston 404 and, in this way, may move piston 404 forward and backward according to the direction of rotation of motor 400. When piston 404 may move to the right, a vacuum may be created, causing intake valve 403, which may be a one-way valve, to let multiple dosages Vi of vaccine flow into the chamber 402, during a filling process.

FIG. 12 shows 5 dosages, V1-V5, in chamber 402. The number of dosages to be stored may be a function of the amount of power and time needed to operate pumping system 390 for multiple dosages versus for a single dosage.

On the other hand, when an injection is to occur, MCU 49 may activate stepper motor 400 to push piston 404 to the left only enough to push the amount of a single dosage Vi. The pressure of the vaccine may cause exit valve 407, which may be a one-way valve, to let vaccine flow into the needle, here labeled 408. MCU 49 may repeat the single dosage injection until chamber 402 may be emptied, at which point, MCU 49 may instruct pumping unit 390 to repeat the filling process.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances or similar electronic computing device that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for mass vaccination, the system comprising:
   a plurality of portable electronic injectors, each comprising:
   at least one needle to administer a measured amount of at least one vaccine to a body tissue;
   an indicator system to provide an indication when either an injection error occurs or when a vaccination indication is required;
   an anti-stabbing mechanism comprising:
   an injection head covering each said at least one needle;
   a switched trigger for a user to retract said injection head away from an active end of said at least needle;
   an inhibitor connected between said switched trigger and said injection head to move said injection head when said switched trigger is activated; and
   a locker to lock said inhibitor in a locking location when said switchwd trigger is not activated;
   a plurality of mobile process managers in wireless communication with said plurality of portable electronic injectors to control a mass vaccination, to receive said vaccination indications, said injection errors and vaccination process data and to alert a vaccination process overseer in generally real-time of said errors; and
   a database in internet communication with at least two of said plurality of mobile process manager to receive said vaccination indications, said injection errors and vaccination process data.

2. The system according to claim 1 and wherein at least one of said plurality of mobile process managers is implemented on one of the following devices:
   a smartphone, a tablet, and a computerized unit.

3. The system according to claim 1 and wherein said wireless communication is a local WI-FI connection.

4. The system according to claim 1 said plurality of mobile process managers also to download injection task parameters to said plurality of portable electronic injectors in parallel.

5. The system according to claim 1 wherein each of said plurality of portable electronic injectors has an associated user unit on which is mounted an indicator light forming part of said indicator system, said indicator light to light up when one of said vaccination indications or injection errors occurs.

6. The system according to claim 1 and wherein said vaccination indications are at least one of: injector status indication, battery level, needle replacement, vaccine low level in each bottle, and number of injection for every injector.

7. The system according to claim 1 and wherein said vaccination process data comprises at least one of: number of injections performed, time to perform them, and temperature of the vaccine at each injection.

8. The system according to claim 1 and wherein at least one of said plurality of process managers also comprises an NFC (near field communication) unit at least to read a unique number associated with each of said portable electronic injectors.

9. The system according to claim 1 and wherein at least one of said plurality of portable electronic injectors also comprises an RFID (radio frequency identification) reader at least to read an RFID tag associated with each animal to be injected.

10. The system according to claim 1 and wherein said switched trigger comprises a mechanical trigger and at least two microswitches connected in series and indicating the movement of said switched trigger and the movement of said injection head.

11. The system according to claim 10 wherein a first of said at least two microswitches detects contact with said mechanical trigger and a second of said at least two microswitches detects contact with said body tissue.

12. The system according to claim 11 and comprising an injection error detection unit to detect when vaccine is flowing and said contact with said body tissue has stopped.

13. The system according to claim 11 and comprising a vibrator to vibrate while injection is still in process.

14. The system according to claim 1 and wherein said inhibitor is a mechanical inhibitor.

15. The system according to claim 1 and wherein at least one of said plurality of portable electronic injectors comprises a heating element located next to said injection head.

16. The system according to claim 15 and wherein said heating element is temperature controlled.

17. The system according to claim 1 and wherein said injector head comprises a stamping pad to mark said body tissue.

18. The system according to claim 1 and wherein at least one of said plurality of portable electronic injectors comprises a spray can and a marking mechanism to activate said spray can to mark said body tissue.

19. The system according to claim 1 and wherein said injector head comprises disinfection material.

20. The system according to claim 1 and wherein said injector head comprises:
   a pair of grabbers to grab skin over said body tissue; and
   a set of hinges per grabber to hold said pair of grabbers closed during a subcutaneous injection and to open said pair of grabbers otherwise.

21. The system according to claim 1 and wherein at least one of said plurality of portable electronic injectors comprises a projector directed towards an injection area to light up said injection area during an injection.

22. The system according to claim 1 wherein said injector head comprises a connector to connect and remove said injector head from said inhibitor.

23. The system according to claim 1 wherein each said injector head comprises:
   a fixed housing with a connection to connect said injection head over said at least one needle to said portable electronic injector;
   a movable housing having an inhibitor connection to connect said movable housing to said inhibitor,
   wherein said fixed and movable housings have a needle housing therein for said at least one needle; and
   a protrusion limiter to define how much said movable housing extends from said fixed housing when said movable housing is moved by said inhibitor thereby to define the length of said at least one needle which protrudes when and injection head is retracted.

24. The system according to claim 1 wherein each said injector head comprises:
   a fixed housing connectable to one of said plurality of portable electronic injectors ;
   a movable housing having a hole on a side thereof;
   a vaccine chamber connectable to vaccine pipes within said one of said plurality of portable electronic injectors, said at least one needle being connected to said vaccine chamber and aligned with said hole; and
   a pressing unit to press said vaccine chamber to the side when said movable housing is pressed into skin of said body tissue, thereby pressing said at least one needle through said side hole and under other portions of said skin.

25. The system according to claim 1 and wherein said at least one needle is two needles and wherein at least one of said plurality of portable electronic injectors comprises a variable position system to vary a distance between said two needles.

26. The system according to claim 1 wherein said database is web-accessible.

27. The system according to claim 26 said database to enable traceability of the vaccination process.

28. The system according to claim 1 wherein each said injector head comprises a protrusion limiter to limit the amount said at least one needle protrudes from said injector head.

29. The system according to claim 1 and comprising a multi-dosage pumping unit to receive multiple dosages of said at least one vaccine and to inject single dosages of said at least one vaccine per injection.

* * * * *